United States Patent [19]

Pramoda et al.

[11] 4,136,173

[45] Jan. 23, 1979

[54] MIXED XANTHAN GUM AND LOCUST BEAM GUM THERAPEUTIC COMPOSITIONS

[75] Inventors: Matura K. Pramoda; Song-Ling Lin, both of Rouses Point, N.Y.

[73] Assignee: American Home Products Corp., New York, N.Y.

[21] Appl. No.: 764,319

[22] Filed: Jan. 31, 1977

[51] Int. Cl.² .................... A61K 35/48; A61K 47/00; A61K 31/35; A61K 31/12

[52] U.S. Cl. .................................... 424/177; 424/181; 424/243; 424/258; 424/300; 424/320; 424/330; 424/331; 424/361

[58] Field of Search ............... 424/361, 105, 181, 300, 424/320, 330, 331, 177, 243, 258

[56] References Cited

U.S. PATENT DOCUMENTS

| | | | |
|---|---|---|---|
| 2,703,777 | 3/1955 | Feinstein et al. | 424/361 |
| 3,416,530 | 12/1968 | Ness | 424/7 |
| 3,640,741 | 2/1972 | Etes | 106/170 |
| 3,659,026 | 4/1972 | Schuppner | 424/361 |
| 3,700,451 | 10/1972 | Sullivan | 96/66 |
| 3,870,791 | 3/1975 | Haddad et al. | 424/361 |
| 3,900,569 | 8/1975 | Monti | 424/361 |
| 3,944,427 | 3/1976 | Sullivan | 106/208 |
| 4,012,333 | 3/1977 | Towler | 424/361 |

FOREIGN PATENT DOCUMENTS 2051369 9/1971 Fed. Rep. of Germany.

OTHER PUBLICATIONS

"The Pharmacopeia of the USA" 18th Revision-9/1/70, pp. 220-221 and 505-506.

J. of Pharm. Sci. 63 (5), 721-724 (1974), Lee et al., "Corneal Absorption of Ophthalmic Drugs".

*Primary Examiner*—Albert T. Meyers
*Assistant Examiner*—D. W. Robinson
*Attorney, Agent, or Firm*—Adley F. Mandel

[57] ABSTRACT

New compositions comprising xanthan gum, locust bean gum, and a pharmaceutical agent in a pharmaceutically acceptable liquid vehicle. More specifically these compositions are useful in drug delivery systems, particularly for ophthalmic drugs.

17 Claims, No Drawings

MIXED XANTHAN GUM AND LOCUST BEAM GUM THERAPEUTIC COMPOSITIONS

BACKGROUND OF THE INVENTION

1. Field of the Invention

This invention relates to a pH sensitive gum composition capable of delivering a pharmaceutical agent in convenient liquid or gel form to its point of application. More particularly, this invention relates to a pharmaceutical delivery system and a method for the controlled administration of drug to a patient. This invention also relates to a pharmaceutical delivery system possessing the property of being liquid at a pH of less than about 3.5–5 and a gel at a pH of greater than about 5. In preferred embodiments, the invention relates to bioerodable drug delivery systems for the controlled administration of drug to a mammalian patient over a prolonged period of time, especially to the eye of such patient. In another aspect the invention relates to the reversibility of the system from liquid to gel and gel to liquid thereby enabling varied methods of application suited to the different biological environments encountered in a mammalian patient. Another aspect of the invention relates to a method for preparing these compositions. A further aspect of this invention relates to the use of these compositions as adjuvants in pharmaceutical formulations to potentiate the response of therapeutic agents.

2. Description of the Prior Art

The prior art is replete with a multiplicity of compositions, products, appliances, applications, dispensers, injectors, depositors for the controlled administration of drug to a mammalian patient. Typically, such products provide a means to carefully regulate the level of drug administration to the patient and also maintain a more uniform and therapeutically effective blood level, thus increasing the effectiveness of the desired treatment.

These products have been in the form of liquids, ointments, tablets, capsules, inserts all and other vehicles having bioerodable properties and/or non-bioerodable properties. Each of these products, depending on its use or application, possess inherent advantages and disadvantages. For example, liquid compositions for dropwise instillation to the eye provide ease of formulation; but accurate administration of the required amount of drug is difficult, as illustrated by the drops of the ophthalmic streaming down the face of the patient during its administration.

Exemplary of insert type drug products are U.S. Pat. Nos. 3,618,604 and 3,867,519. The former illustrates the non-bioerodable type of ocular insert for controlled drug administration while the latter teaches the use of a bioerodable ocular insert. These inventions, however, require relatively detailed and complex preparatory techniques. Furthermore, with both types of inserts, the patients may suffer irritation, discomfort, dislocation and/or bacterial contamination via their placement or migration within the eye.

Other disadvantages associated with the non-bioerodable drug product, device, or vehicle are more apparent when such devices are employed in areas of the anatomy other than the eye, and surgical or other professional removal is necessary.

Tablets and the like, whether or not bioerodable, suffer the inherent disadvantages of solid preparation techniques.

In other aspects of drug products vehicles and compositions, the prior art teaches the use of various gums and polymers to potentiate the pharmacological response of drugs. In this connection, for example, the use of methyl cellulose, hydroxymethyl cellulose, guar gum, polyvinyl alcohol, diethylaminoethyl dextran, alginic acid and others is familiar to those skilled in the art. Some of these gums, polymers, and others are also used in eye preparations.

U.S. Pat. Nos. 3,557,016 and 3,519,434, disclose the making of a heat reversible aqueous gel composition, containing xanthan and locust bean gums, and its application to various food preparations. These disclosures, however, do not teach that reversible gel compositions of these gums, sensitive to factors other than heat, can be prepared nor how to use such compositions in drug delivery or as a vehicle. U.S. Pat. Nos. 3,700,451 and 3,944,427 disclose gelable and gelled compositions containing a liquid medium, agar and a combination of xanthan and locust bean gums. These compositions are said to be useful to process photosensitive media and as a carrier for therapeutic agents. These compositions, however, will not produce reversible liquid-gel properties dependent on pH variability, but are gels at all disclosed concentrations.

SUMMARY OF THE INVENTION

The present invention relates to a pH sensitive composition comprising a xanthan gum and locust bean gum solution in a pharmaceutically acceptable liquid vehicle, said composition having reversible properties as will be illustrated.

Another aspect of this invention relates to a composition comprising xanthan gum and locust bean gum in combination with a pharmaceutical agent (for convenience pharmaceutical agent, drug, and medicament will be used interchangably).

Still another aspect of this invention relates to the use of said gum compositions in drug delivery and vehicles.

In this specification a "gel" is defined as a colloid in which the disperse phase has combined with the continuous phase to produce a semi-solid such as a jelly. The gel will usually form as an elastic bead or a doughnut shaped ring when in contact with the described pH environment. Also, the meaning of the term bioerodable includes physically erodable.

DETAILED DESCRIPTION OF THE INVENTION

In this application "xanthan gum" means Xanthomonas hydrophilic colloid produced by bacteria of the genus Xanthomonas. Illustrative of such a colloid is the xanthan gum sold under the Keltrol trademark (Kelco Co., Clark, N.Y.). It may be described as a high molecular weight natural carbohydrate, or more specifically polysaccharide. The generic term xanthan gum defines exocellular biopolysaccharides which are produced in a pure culture fermentation process by the microorganism Xanthomonas campestris. Three different monosaccharides are found in the basic structure - mannose, glucose and glucuronic acid (as a mixed potassium, sodium and calcium salt). Each repeating block within the polymer contains sixteen sugar units. The linear portion consists of five, 1 →→→ 4-linked D-glucose units, four, 1 →→→ 4-linked D-mannose units and four, 1 →→→ 2-linked D-glucuronic acid units. At C-3 of two glucose units there are mannose branches and at some other position, as yet undetermined, in the repeating unit is a side chain derived from pyruvic acid and glucose i.e. 4,6-O-(carboxyethylidine)-D-glucose. Each repeating unit contains an average of 3.4 acetyl groups which are believed to be connected at $C_6$ of mannose.

Locust bean gum is a high molecular weight polysaccharide derived from ceratonia siliqua. Chemically, locust bean gum is a galactomannan best illustrated with galactose units located on every fourth mannose unit, with smaller amounts of pentoglycan, protein, cellulose and ash. A detailed description of the composition, physical and chemical properties, preparation, etc. of locust bean gum is given in Industrial Gums (Polysaccharides and Their Derivatives), Academic Press, (1959) at pp. 361–376, incorporated herein by reference.

The present invention relates to a composition of matter comprising a solution of plant seed gum and microbial gum in a liquid vehicle wherein the pH of the solution is adjusted, depending on the application, to a pH of less than about 3.5–5 for liquid administration, and to a pH of greater than about 5 for gel administration. Because of its pH sensitive properties, this invention has proved adaptable to its administration in convenient liquid form such that the composition reverts to a gel upon contact with an environment where the pH is greater than about 5. This invention is most useful as a vehicle for the controlled administration of a predetermined dosage regimen of drug.

It is to be understood that the change in the physical state of the solution is a gradual one. The critical pH at which the change can be observed is dependent on the total gum concentration and on the concentration of xanthan gum in the mixed gum system. As a general rule, as the total gum concentration increases, the pH at which the liquid to gel transformation begins will decrease. Insofar as the effect of the xanthan gum concentration in the xanthan-locust bean gum mixed system on reversibility, it is observed that this effect is less significant than that of total gum concentration. It can be stated, however, that the liquid to gel transformation begins at a lower pH when the concentration of xanthan gum in the mixed gum system is about 40–60% than when it is outside these concentrations.

In a preferred embodiment, the formulations of this invention are administered topically to the eye in the form of ophthalmic solutions.

The concentrations of ingredients in these formulations are expressed as percent weight by volume, unless noted otherwise. In preferred compositions, the plant seed gum is locust bean gum and the microbial gum is xanthan gum, and generally the total gum concentration in solution is from about 0.01% to about 1%. It is preferred to keep the total gum level in solution at about 0.1% to about 0.5%.

The use of the lower concentration of the mixed gums will usually depend on whether the gums are used to potentiate a drug's pharmacologic response as described below or whether a gelable composition is sought. In the former case, as little as 0.01% gum concentration in solution will be satisfactory depending on the drug. Where gelable compositions are required, a minimum of about 0.1% to about 0.15% gum concentration in solution is preferrable.

In these gelable compositions, furthermore, the proportions of the respective xanthan and locust bean gums is important. The percent of xanthan gum in the mixed gum system ranges from about 6% to about 94% of the total gum content, the remainder being locust bean gum.

In concentrations outside this range or in solutions containing only one of these gums, sufficient gelling did not occur, nor, at the same time did these solutions demonstrate pH sensitive liquid-gel reversibility. However, in compositions formulated solely to potentiate a drug's pharmacologic response, the xanthan gum concentration in the mixed xanthan gum-locust bean gum system ranges from about 1% to about 99% of the total gum content. The preferred concentration of xanthan gum in the mixed gum system for both the gelable composition and the potentiated composition is from about 40% to about 60%, the remainder being locust bean gum.

Because it has been found that the pH sensitive liquid-gel properties of the composition are not appreciably altered by incorporating therapeutically effective amounts of drug, the compositions of this invention can be used as a drug vehicle. In the case of ophthalmic use, drug containing compositions of this invention can be administered by dropwise instillation. Concentrations of drug in the formulations of this invention vary with the specific drug employed, so long as a therapeutically effective dosage is incorporated.

In an especially preferred embodiment, the compositions of this invention can be combined with echothiophate iodide to provide a longer acting formulation. Thus, an advantage of the present invention is that in treating a disease condition, the daily regimen of drug administration is significantly reduced in comparison with other drug vehicles.

Activity increases with increased concentration of the therapeutic agent employed in the formulations of this invention. Such concentrations generally fall within the above described ranges; however, it is to be understood that these general ranges may be modified in certain instances to suit the needs and responses of an individual patient. Therefore, any dose which will produce the desired effect without irritation can be used. It has been found, however, that the incorporation of the described gums in the drug system potentiate a greater pharmacological response than in systems not having the gum, thus allowing effective lower dosages to be administered, particularly, in ophthalmic compositions. By way of example, gum containing ophthalmic compositions of echothiophate iodide activated about the same miotic response in the eyes of rabbits as did ophthalmic compositions containing much higher dosages of echothiophate iodide. Similar tests indicate that the dose of pilocarpine can be reduced by one fifth with the use of the herein described gum compositions. Thus, the compositions described and contemplated within this invention may be used simultaneously or alternately as a vehicle for delivering a drug and as an adjuvant for various drugs, particularly, ophthalmic drugs.

Although the ophthalmic drug compositions of this invention can be administered in a sterile physiological saline vehicle, in many cases it is preferred to formulate these compositions into an ophthalmic vehicle. Such vehicles are well known in the art and are fully described in such standard reference works as Remington's Pharmaceutical Sciences, Martin and Cook, Map Publishing Company, Easton, Pa., 13th Edition (1965).

While the compositions of this invention are particularly well suited to the administration of water soluble drug, it will be appreciated that it is equally well adapted to the administration of drugs which are not water soluble. By way of illustration, these compositions maintain their pH sensitivity in the presence of such non-aqueous solvents as ethanol, propylene glycol, 1,3-butanediol, glycerin, sorbitol and the like when such solvents compose up to about one third by volume of the carrier system, i.e., the liquid vehicle comprises 60-100% water.

The compositions of this invention can be designed by first selecting the drug to be used, the pharmacological response desired, the dosage needed to produce that level of pharmacological response, and the period of therapy. A composition can then be designed to produce that pharmacological response comprising the mixed gums and the selected drugs.

Any of the drugs used to treat the eye and surrounding tissues can be incorporated in the ophthalmic compositions of this invention.

Suitable drugs for use in therapy of the eye with the ophthalmic compositions of this invention, consistent with their known dosages and uses, are without limitation; antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and sulfisoxazole; antiallergenics such as antazoline, methapyriline, chlorpheniramine, pyrilamine and prophenpyridamine; anti-inflammatories such as cortisone, hydrocortisone, hydrocortisone acetate, dexamethasone, deamethasone 21-phosphate, fluocinolone, medrysone, prednisolone, methylpredenisolone, predisolone 21-phosphate, prednisolone acetate, prednisone, fluoromethalone, betamethasone and triamcinolone; decongestants such as phenylephrine, naphazoline, and tetrahydrazoline; miotics and anticholinesterases such as pilocarpine, eserine salicylate, carbachol, diisopropyl fluorophosphate, dibenamine, tolazoline, echothiophate iodide, and demecarium bromide; mydriatics such as atropine sulfate, cyclopentolate, homatropine, scopolamine, tropicamide, eucatropine and hydroxyamphetamine; and sympathomimetics such as epineprine, cocaine, and ephedrine.

The above drugs and other drugs can be present in the composition alone or in combiantion form with pharmaceutical carriers for the various routes of drug administration described in this application. The carriers acceptable for the purpose of this invention are the art-known carriers that do not adversely affect the drug, the host, or the material comprising the drug delivery device. Suitable pharmaceutical carriers include sterile water; electrolytes such as NaCl; dextrose; dextrose in water or saline; lower alkanols; oils such as corn oil; peanut oil; sesame oil, and the like, with emulsifiers such as mono- or di-glyceride of a fatty acid, or a phosphatide, e.g., lecithin, and the like; glycols; aqueous media in the presence of a suspending agent, for example, sodium carboxymethylcellulose; sodium alginate; polyvinylpyrrolidone; and the like, alone, or with a suitable dispersing agent such as lecithin, polyoxyethylene stearate; and the like. The carrier may also contain adjuvants such as preserving, stabilizing, wetting, emulsifying agents, and the like.

In preferred embodiments, the ophthalmic composition is intended to provide a complete dosage regimen for eye therapy over this prolonged period. Therefore, the amount of drug to be incorporated in the composition is determined by the fact that sufficient amounts of drug must be present to maintain the desired pharmacological response over the therapeutic treatment period. Illustratively, in order to treat glaucoma in an adult human, the daily release dosage should be in the range of between 25 micrograms to 1,000 micrograms or pilocarpine per day, levels which may now be modified downward, as discussed earlier, due to the potentiation of miotic response made possible by the gums.

Although the use of the drug delivery systems of this invention has principally been described with regard to ophthalmic compositions for the controlled administration of ophthalmic drugs to the eye, these materials may be employed as well in a wide variety of compositions for administering drugs at a controlled rate to other areas of the body which offer biological environment of suitable pH required to affect the gel effect or that are susceptible to potentiation by the mixed gum system. Thus, the pharmaceutical delivery systems of this invention may be employed to advantage in external and internal bioerodable drug delivery compositions such as, for example, topical, oral, nasal and buccal preparations; peroral dosage forms which bioerode by the action of the saline in saliva; subcutaneous implants for releasing a drug to the tissue of a patient; vaginal preparations and rectal preparations which are eroded by the action of vaginal and intestinal fluids respectively. In each instance, the composition employs xanthan and locust bean gum in combination and is of a shape or form appropriate for administering in the described body tissues or cavities respectively or for application to a particular body area.

Therefore, in practicing the invention, one can employ any drug used to treat the body in addition to those ophthalmic drugs previously listed, which is capable of being dispersed in or confined by the resultant gel composition in accordance with the above-described invention and with the known usages of the drug.

The term "drug" as used herein is intended to be interpreted in its broadest sense as including any composition or substance that will produce a pharmacologic response, either at the site of application or at a site remote therefrom. Suitable drugs for use in therapy with the drug delivery systems of the invention include without limitation:

1. Protein drugs such as insulin;
2. Desensitizing agents such as ragweed pollen antigens, hay fever pollen antigens, dust antigen and milk antigen;
3. Vaccines such as small pox, yellow fever, distemper, hog cholera, fowl pox, anti-venom, scarlet fever, diphtheria toxoid, tetanus toxoid, pigeon pox, whooping cough, influenzae, rabies, mumps, measles, poliomyelitis, Newcastle disease, etc.;
4. Anti-infectives, such as antibiotics, including penicillin, tetracycline, chlortetracycline, bacitracin, nystatin, streptomycin, neomycin, polymyxin, gramicidin, oxytetracycline, chloramphenicol, and erythromycin; sulfonamides, including sulfacetamide, sulfamethizole, sulfamethazine, sulfadiaaine, and sulfisoxazole, antivirals including idoxuridine; and other anti-infectives including nitrofurazone and sodium propionate;
5. Anti-allergencies such as antazoline, methapyrilene, chlorpheniramine, pyrilamine and prophenpyridamine;
6. Anti-inflammatories such as hydrocortisone, cortisone, hydrocortisone acetate, dexamethasone, dexamethasone 21-phosphate, fluocinolone, triamcinolone, medrysone, prednisolone, prednisolone 21-phosphate, and prednisolone acetate;
7. Decongestants such as phenylephrine, naphazoline, and tetrahydrozoline;

8. Sympathomimetics such as epinephrine;
9. Sedatives and Hypnotics such as pentobarbital sodium, phenobarbital, secobarbital sodium, codeine, (α-bromoiso-valeryl) uera, carbromal;
10. Physchic Energizers such as 3-(2-aminopropyl)indole acetate and 3-(2-aminobutyl)Indole acetate;
11. Tranquilizers such as reserpine, chlorpromazine, and thiopropazate;
12. Androgeic steroids such as methylestosterone and fluoxymesterone;
13. Estrogens such as estrone, 17 β-estradiol, ethinyl estradiol, and diethyl stilbesterol;
14. Progestational agents such as progesterone, megestrol, melengestrol, chlormadinone, ethisterone, norethynodrel, 19-norprogesterone, norethindrone, medroxyprogesterone and 17 α-hydroxyprogesterone;
15. Hormonal agents such as the prostaglandins, for example, $PGE_1$, $PGE_2$;
16. Antipyretics such as asprin, sodium salicylate, and salicylamide;
17. Antispasmodics such as atroine, methantheline, papaverine, and methscopolamine bromide;
18. Anti-malarials such as the 4-amino-quinolines, 8-amino-quinolines, chloroquine, and pyrimethamine;
19. Antihistamines such as diphenhydramide, dimenhydrinate, tripelennamine, perphenazine, and carphenazine;
20. Cardioactive agents such as hydrochlorothiazide flumethiazide, chlorothiazide, and aminotrate;
21. Nutritional agents such as vitamins, essential amino acids and essential fats;
22. Anti-Parkinsonism agents such as L-dopa, (1-3,4-dihydroxyphenylalanine);
23. Investigative antihypotensive agents such as dopamine, 4-(2-aminoethyl)pyrocatechol.

The amount of drug employed in compositions in accord with this invention may vary over a wide range depending upon the type of drug and the dosages desired. The amount may vary from the minimum effective single dosage of the drug employed to a maximum number of effective doses limited only by the release characteristics of the composition of this invention. In general, drug is usually present in an amount sufficient for a terapeutically effective dosage.

Additionally, the ophthalmic compositions may include the following: preservatives, including chlorobutanol, benzyl alcohol, phenylethyl alcohol, parabens, benzalkonium chloride, and benzethonium chloride buffers, including acetates, lactates, borates, citrates and phosphates; electrolytes, such as sodium chloride, potassium chloride and calcium chloride; antioxidants, such as sodium bisulfite, sodium thiosulfate and cysteine; stabilizers, including EDTA, Polysorbate 20 and Polysorbate 80; and vehicles including water and others as listed earlier.

For a more complete understanding of the compositions contemplated by this invention and their methods of preparation, reference should be made to the following examples. It is to be understood that these examples are given merely as further illustrations of the invention, and are not to be construed in a limiting sense.

EXAMPLE 1

The formulations listed below

| | | |
|---|---|---|
| Locust Bean Gum[1] | 3 | g |
| Xanthan Gum[2] | 2 | g |
| Sodium Phosphate | 0.26 | g |
| Boric Acid | 0.6 | g |
| Mannitol U.S.P. | 12 | g |
| Chlorobutanol Anhydrous | 5.0 | g |
| Hydrochloric Acid Q.S. to pH 3 | 2 | ml |
| Distilled Water Q.S. | 1 | liter |

[1]SUPERCOL ® locust bean gum has been used, a product of Soluble Products Corp., but other locust bean gums are compatible, such as SEAGEL ® from Marine Colloids Inc., also used.
[2]Xanthan gum used, was usually KELTROL ®, a product of Kelco Company, but other xanthan gums are compatible.

has been prepared in the following manner:
1. Place 900 ml of water in a suitable container equipped with a dispersator.
2. Place 30 ml of Distilled Water in a Blender and add the Anhydrous Chlorobutanol. Blend for 2 minutes at low speed. Add this dispersion to Step No. 1 with stirring.
3. Add the Mannitol, Boric Acid and Dried Sodium Phosphate to Step No. 2 and stir until completely dissolved.
4. Blend the Locust Bean Gum and Xanthan Gum with the solution for about 10 minutes.
5. Add 2 ml of 1N Hydrochloric Acid to the solution and filter.
6. Bring the batch to volume with Distilled Water.

EXAMPLE 2

An ophthalimic composition employing a pH sensitive reversible gel solution was prepared as in Example 1, but after adjusting for pH filtering, dissolved echothiophate iodide and potassium acetate (if used) to prepare test solution.

In this manner the following formulations were prepared for testing:

TABLE I

| Ingredients | A | B | C | D |
|---|---|---|---|---|
| Echothiophate Iodide | 0 | 0.3 GM | 2.5 GM | 0.3 GM |
| Locust Bean Gum | 3 GM | — | — | 3 GM |
| Xanthan Gum | 2 GM | — | — | 2 GM |
| Sodium Phosphate Dried | 0.25 GM | 0.26 GM | 0.25 GM | 0.26 GM |
| Boric Acid Reagent Grade | 0.60 GM | 0.60 GM | 0.60 GM | 0.60 GM |
| Mannitol | 12 GM | 12 GM | 12 GM | 12 GM |
| Potassium Acetate | — | 8 GM | 8 GM | — |
| Chlorobutanol Anhydrous | 5 GM | 5 GM | 5 GM | 5 GM |
| Hydrochloric Acid, Q.S. to pH3 | | — | — | |
| Distilled Water Q.S. | 1 Liter | 1 Liter | 1 Liter | 1 Liter |

Table II

| Ingredients | E | F | G | H | I |
|---|---|---|---|---|---|
| Echothiophate Iodide | 0.3 gm | 0.3 gm | 0.1 gm | 0.1 gm | 0.1 gm |
| Locust Bean Gum | 3 gm | 0.6 gm | 4 gm | 3 gm | 1 gm |
| Xanthan Gum | 2 gm | 0.4 gm | 1 gm | 2 gm | 4 gm |
| Phenylethyl Alcohol | — | — | 5 ml | 5 ml | 5 ml |
| Hydrochloric Acid, Q.S. to pH3 | | | | | |
| Distilled Water Q.S. | 1 Liter | 1 Liter | 1 Liter | 1 Liter | 1 liter |

Rabbit's eyes were treated with 2 drops of the test solution, and pupillary diameters were measued with a cathetometer. The miotic response intensity was computed by taking the difference in pupillary diameters at zero time and time "T" (i.e., hours after instillation) and dividing it by the pupillary diameter at zero time. The table below illustrates the average miotic response for all eyes as a function of hours after instillation.

|   | *AMI at HOURS AFTER INSTILLATION | | | | | |
|---|---|---|---|---|---|---|
|   | 1 | 2 | 3 | 7 | 24 | 25 |
| A | 0.03 | 0.05 | 0.09 | 0.00 | 0.03 | 0.04 |
| B | 0.01 | 0.02 | 0.07 | 0.05 | 0.13 | 0.18 |
| C | 0.14 | 0.44 | 0.45 | 0.49 | 0.39 | 0.33 |
| D | 0.36 | 0.62 | 0.70 | 0.57 | 0.26 | 0.26 |
| E | 0.55 | 0.57 | 0.64 | 0.58 | 0.45 | 0.52 |
| F | 0.53 | 0.61 | 0.65 | 0.57 | 0.32 | 0.40 |
| G | 0.25 | 0.43 | 0.48 | 0.30 | 0.20 | 0.21 |
| H | 0.45 | 0.50 | 0.53 | 0.32 | 0.31 | 0.28 |
| I | 0.44 | 0.53 | 0.57 | 0.39 | 0.28 | 0.26 |

*Avg. Miotic Response Intensity

By comparing formulations D-I inclusive with formulations B and C, it is clear that the former group potentiated significantly higher miotic response intensities than those formulations not having the combined gums. Thus, it was observed that the dosage level of gum containing formulations can be reduced. It was also observed that the gum containing formulations could be used to deliver a sustained and controlled dosage regimen of echothiophate iodide over a 24 hour period.

EXAMPLE 3

Formulations containing pilocarpine hydrochloride were prepared as in Example 2 and are illustrated as follows:

TABLE III

| Ingredients | J | K | L |
|---|---|---|---|
| Pilocarpine Hydrochloride | 0.1 GM | 0.5 GM | 0.1 GM |
| Locust Bean Gum | — | — | 3 GM |
| Xanthan Gum | — | — | 2 GM |
| Boric Acid | 12.4 Gm | 12.4 GM | 12.4 GM |
| Potassium Chloride | 0.4 GM | 0.4 GM | 0.4 GM |
| Sodium Carbonate Q.S. to pH3 | | | — |
| Hydrochloric Acid Q.S. to pH3 | — | — | |
| Distiller Water Q.S. | 1 Liter | 1 Liter | 1 Liter |

Rabbits' eyes were treated and tested as in Example 2, the results are listed in the following table.

|   | AMI AT HOURS AFTER INSTILLATION | | | | |
|---|---|---|---|---|---|
|   | 0.3 | 0.7 | 0.8 | 1 | 2 |
| J | — | 0.01 | 0.01 | 0.1 | — |
| K | 0.08 | 0.25 | 0.22 | 0.27 | 0.08 |
| L | 0.08 | 0.20 | 0.22 | 0.14 | 0.05 |

These results indicated that the gums potentiate the miotic response of pilocarpine hydrochloride. It therefore appears that the dose of pilocarpine can be reduced up to one fifth with the combined use of locust bean and xanthan gums.

EXAMPLE 4

Formulations containing the aldose reductase inhibitor, 1,3-dioxo-1H-benz [de] isoquinoline-2(3H)-acetic acid, Alrestatin ® were prepared as in Example 2:

|   | W | X |
|---|---|---|
| Alrestatin | 12.0 g | 12.0 g |

-continued

|   | W | X |
|---|---|---|
| Potassium Hydroxide | 3.25 g | 3.35 g |
| Locust Bean Gum | — | 0.50 g |
| Xanthan Gum | — | 0.50 g |
| Benzalkonium Chloride at 17% | 0.06 ml | 0.06 ml |
| EDTA Acid | 0.10 g | 0.10 g |
| Potassium Hydroxide Q.S. to pH6 | | |
| Phenylethyl Alcohol | — | 1.0 ml |
| Distilled Water Q.S. to | 100 ml | 100 ml |

Potentiation of the aldose reductase inhibitor was demonstrated by measuring its ocular penetration following instillation in the eyes of unanesthesized rabbits, see below:

TABLE
OCULAR PENETRATION OF ALRESTATIN

|   | W | X |
|---|---|---|
| Aqueous Humor (mcg/ml) | 8.5 | 11.8 |
| Cornea (mcg/g) | 78 | 160 |
| Len (mcg/g) | 0.5 | 0.6 |

These results illustrate increased ocular penetration in formulation containing locust bean and xanthan gums in combination with aldose reductase inhibitor.

EXAMPLE 5

I. — Formulations containing the polypeptide, gonadorelin also known as luteinizing hormone-releasing hormone (LH-RH) were evaluated for potency.

| Formula per liter | |
|---|---|
| LH-RH | Varied |
| Locust Bean Gum | 3 gms |
| Xanthan Gum | 2 gms |
| Chlorobutanol | 5 gms |
| Hydrochloric Acid Q.S. to pH 3 | |
| Distilled Water Q.S. to | 1 Liter |

Prepared by hydrating each gum separately at 80° C. for 30 minutes and treated with a cell disrupter for 2 minutes. The gum solutions were mixed in the presence of hydrochloric acid by adjusting the pH to 3. Chlorobutanol was then dissolved in the mixed gum solution and filtered. LH-RH was then dissolved in the gum solution over a dose range of 0 to 500 nanograms.

The test solutions were administered subcutaneously to neuroleptically treated rats. The number of rats ovulating and the number of ova at different LH-RH dose levels is shown in the following table.

| Dose of AY-24,031 Administered in NG | Number Of Rats Ovulating | | Number of Ova Found | |
|---|---|---|---|---|
|   | Control (No Gums) | with 0.5% Gums | Control (No Gums) | With 0.5% Gums |
| 0 | 0/10 | 0/10 | 0 | 0 |
| 31 | 0/10 | 0/10 | 0 | 0 |
| 62 | 2/10 | 3/10 | 7 | 8.7 ± 1.4 |
| 125 | 5/10 | 7/10 | 8 ± 1.2 | 10.6 ± 0.6 |
| 250 | 8/10 | 9/10 | 10.1 ± 0.5 | 11.2 ± 0.7 |
| 500 | 10/10 | 10/10 | 10.5 ± 0.6 | 11.5 ± 0.5 |

These results indicate that LH-RH has been released from the site of injection (s.c.) and reached the target organ (pituitary) where it released LH and subsequently induced ovulation in fluphenazine dihydrochloride (FD) pre-treated proestrous rats.

II. — Formulations containing 2% LH-RH, 0.25% locust bean gum, 0.25% xanthan gum, and 0.5–1% phenylethyl alcohol were also prepared and evaluated intranasally. Results indicate that the intranasal method of administration also stimulates LH-RH release at a level greater than formulations without the mixed gums.

EXAMPLE 6

Formulations containing Neomycin sulfate and/or dexamethasone were evaluated for stability.

TABLE IV

| Formula Per Liter | N | O | P |
|---|---|---|---|
| Neomycin Sulfate | 3.5 gm | 3.5 gm | — |
| Dexamethasone | 1.0 gm | — | 1.0 gm |
| Locust Bean Gum | 1.5 gm | 1.5 gm | 1.5 gm |
| Xanthan Gum | 1.0 gm | 1.0 gm | 1.0 gm |
| Phenylethyl Alcohol | 5.0 ml | 5.0 ml | 5.0 ml |
| Distilled Water Q.S. to | 1 Liter | 1 Liter | 1 Liter |

Manufactured as described in Example 2, the stability (of these formulations) was monitored over a 3 month period and no significant changes were noted.

EXAMPLE 7

Formulations containing phenylephrine HCl and/or prednisolone acetate were evaluated for stability.

TABLE V

| Formula Per Liter | Q | R | S |
|---|---|---|---|
| Phenylephrine HCL | 2.5 gm | 2.5 gm | — |
| Prednisolone Acetate | 5.0 gm | — | 5.0 gm |
| Tween 80 | 1.0 gm | 1.0 gm | 1.0 gm |
| Locust Bean Gum | 1.5 gm | 1.5 gm | 1.5 gm |
| Xanthan Gum | 1.0 gm | 1.0 gm | 1.0 gm |
| Phenylethyl Alcohol | 5.0 ml | 5.0 ml | 5.0 ml |
| Distilled Water Q.S. to | 1 Liter | 1 Liter | 1 Liter |

Manufactured as described in Example 1, these formulations were monitored for stability over a 3 month period and no significant changes were noted.

EXAMPLE 8

Manufactured as described in Example 1, the stability of a formulation containing epinephrine bitartarate was assessed over a 3 month period and found to be satisfactory.

| Formula Per Liter | |
|---|---|
| Epinephrine Bitartarate | 20 gm |
| Locust Bean Gum | 1.5 gm |
| Xanthan Gum | 1.0 gm |
| Phenylethyl Alcohol | 5.0 ml |
| Distilled Water Q.S. to | 1 Liter |

EXAMPLE 9

Manufactured as described in Example 1, the stability of formulations containing phenylephrine HCl and/or sulfactamide sodium was assessed over a 3 month period and found to be satisfactory.

| Formula Per Liter | | |
|---|---|---|
| Sulfacetamide Sodium | 150 gm | 300 gm |
| Phenylephrine HCl | 1.25 gm | — |
| Locust Bean Gum | 1.5 gm | 1.5 gm |
| Xanthan Gum | 1.0 gm | 1.0 gm |
| Phenylethyl Alcohol | 5.0 ml | 5.0 ml |
| Distilled Water Q.S. to | 1 Liter | 1 Liter |

EXAMPLE 10

The following formulations demonstrated the pH reversibility of gum containing solutions in the presence of non-aqueous solvents.

In each case a 1% weight/volume solution of the individual gum was prepared by first dispersing the gum in distilled water, autoclaving the resultant solution for 1 hour, filtering, adding 1% of phenylethyl alcohol and bringing the solution to volume. The mixed gum solution was then preferably prepared w/mixing by adding 10 ml of a non-aqueous solvent to 10 ml of a 1% weight-/volume xanthan gum solution, followed by the addition of 10 ml of the 1% weight/volume locust beam gum solution. These solutions, being neutral, formed a gel which liquified with the addition of 1 ml of 0.1 N HCl. Thus, pH reversible gum containing solutions with such non-aqueous solvents as ethanol, propylene glycol, 1,3-butanediol, glycerine, sorbitol, and the like could be prepared.

EXAMPLE 11

Manufactured as described in Example 1, formulations containing carbachol, 2-[(Aminocarbonyl)oxy]-N,N,N-trimethylethanaminium chloride were prepared.

| Formula per 50 ml | | |
|---|---|---|
| Carbachol | 0.50 g | 1.50 g |
| Phenylethyl Alcohol | 0.125 ml | 0.125 ml |
| Xanthan Gum | 0.125g | 0.125g |
| Locust Bean Gum | 0.125g | 0.125g |
| Distilled Water q.s. to | 50 ml | 50 ml |
| Hydrochloric Acid q.s. to pH 3 | √ | √ |

The stability of carbachol containing formulations were evaluated and found to be satisfactory.

We claim:

1. A pharmaceutical composition consisting essentially of a pH sensitive solution of a pharmaceutically acceptable liquid vehicle of xanthan gum, locust bean gum and a therapeutically effective amount of a pharmaceutically active drug in said vehicle; wherein said mixed gums together comprise about 0.01–1.0% weight by volume of the liquid composition; and wherein the percent of xanthan gum in the mixed gums is from about 6–94% of the total gum content, the remainder being locust bean gum; said composition being a liquid at a pH of less than about 3.5–5 and a gel at a pH above about 5; and wherein said liquid vehicle comprises 60–100% water by volume.

2. The composition of claim 1 wherein said gums comprise about 0.15–0.5% of the liquid composition.

3. The composition of claim 1 wherein the percent of xanthan gum in the mixed gums is from about 40–60% of the total gum content, the remainder being locust bean gum.

4. The composition of claim 1 wherein said drug is an ophthalmically active drug.

5. The composition of claim 4 wherein said drug is echothiophate iodide.

6. The composition of claim 4 wherein said drug is pilocarpine hydrochloride.

7. The composition of claim 4 wherein said drug is at least one selected from the group consisting of phenylephrine hydrochloride, prednisolone acetate and sulfacetamide sodium.

8. The composition of claim 4 wherein said drug is epinephrine bitartarate.

9. The composition of claim 4 wherein said drug is the aldose reductase inhibitor 1,3-dioxo-lH-benz-[de]isoquinoline-2(3H)-acetic acid.

10. The composition of claim 4 wherein said drug is carbachol.

11. The composition of claim 1 wherein said drug is gonadorelin.

12. The composition of claim 1 wherein said drug is at least one selected from the group consisting of neomycin sulfate and dexamethasone.

13. An ophthalmic composition for the administration of a drug to the eye consisting essentially of a pH sensitive solution in a pharmaceutically acceptable liquid vehicle of about 0.04% to about 0.4% xanthan gum, about 0.06% to about 0.4% locust bean gum, wherein said gums together comprise about 0.1% to about 0.5% of said composition; about 0.01% to about 0.25% of echothiophate iodide; wherein the pH of said composition is adjusted to a pH of less than about 3.5-5, said percentages being expressed as weight per volume and wherein said liquid vehicle comprises 60-100% water by volume.

14. An ophthalmic composition for the administration of a drug to the eye in a pharmaceutically acceptable liquid vehicle consisting essentially of about 0.1% to about 0.4% of xanthan gum, about 0.1% to about 0.4% of locust bean gum, wherein said gums together comprise about 0.2% to about 0.5% of said composition; about 0.01% to about 0.05% of pilocarpine; and wherein the pH of said composition is adjusted to a pH of less than about 3.5-5, said percentages being expressed as weight per volume and wherein said liquid vehicle comprises 60-100% water by volume.

15. An opthalmic composition consisting essentially of a pH sensitive solution in a pharmaceutically acceptable liquid vehicle of about 0.5% of xanthan gum; about 0.5% of locust bean gum; and a therapeutically effective dosage of 1,3-dioxo-lH-benz[de]isoquinoline-2(3H)-acetic acid; wherein the pH of said liquid composition is greater than about 5; and wherein said percentage is expressed as weight per volume; and wherein said liquid vehicle comprises 60-100% water by volume.

16. A method for increasing the effectiveness in a mammalian patient of a therapeutically effetive amount of a drug in a topically administered liquid composition which consists essentially of incorporating within said composition an adjuvantally effective amount of xanthan gum and locust bean gum.

17. An ophthalmic composition for the administration of drug to the eye in a pharmaceutically acceptable liquid vehicle consisting essentially of about 0.1% to about 0.4% of xanthan gum, about 0.1% to about 0.4% of locust bean gum, wherein said gums together comprise about 0.2% to about 0.5% of said composition; and a therapeutically effective dosage of carbachol; wherein the pH of said composition is adjusted to a pH of less than about 3.5-5, said percentages being expressed as weight per volume; and wherein said liquid vehicle comprises 60-100% water by volume.

* * * * *